United States Patent

Stine et al.

[11] Patent Number: 5,990,367
[45] Date of Patent: *Nov. 23, 1999

[54] PROCESS FOR OLIGOMER PRODUCTION AND SATURATION

[75] Inventors: Laurence O. Stine, Western Springs; Brian S. Muldoon, Mt. Prospect; Steven C. Gimre, Carol Stream; Robert R. Frame, Glenview, all of Ill.

[73] Assignee: UOP LLC, Des Plaines, Ill.

[*] Notice: This patent is subject to a terminal disclaimer.

[21] Appl. No.: 09/187,699

[22] Filed: Nov. 6, 1998

Related U.S. Application Data

[63] Continuation-in-part of application No. 08/990,828, Dec. 15, 1997, Pat. No. 5,895,830, which is a continuation-in-part of application No. 08/573,314, Dec. 15, 1995, abandoned.

[51] Int. Cl.$^6$ ..................................... C07C 2/18
[52] U.S. Cl. .................. 585/514; 585/502; 585/504; 585/506; 585/509
[58] Field of Search ..................... 585/502, 504, 585/506, 509, 514

[56] References Cited

U.S. PATENT DOCUMENTS

| | | | |
|---|---|---|---|
| 2,526,966 | 10/1950 | Oberfell et al. | 196/1 |
| 4,200,714 | 4/1980 | Mahoney et al. | 526/68 |
| 4,254,294 | 3/1981 | Juguin et al. | 585/525 |
| 4,304,948 | 12/1981 | Vora et al. | 585/315 |
| 4,393,259 | 7/1983 | Ward et al. | 585/315 |
| 4,678,645 | 7/1987 | Chang et al. | 422/190 |
| 4,749,820 | 6/1988 | Kuo et al. | 585/330 |
| 5,049,360 | 9/1991 | Harandi et al. | 422/141 |

FOREIGN PATENT DOCUMENTS 2186287  2/1987  United Kingdom.

*Primary Examiner*—Bekir L. Yildirim
*Attorney, Agent, or Firm*—Thomas K. McBride; John G. Tolomei

[57] ABSTRACT

A process for the production of $C_8$ and higher olefins by the oligomerization of light olefins to heavier olefins is improved by the addition of heavy paraffins to the oligomerization zone. The recycle of the heavy paraffins extends the catalyst activity and improves the catalyst life.

24 Claims, 1 Drawing Sheet

PROCESS FOR OLIGOMER PRODUCTION AND SATURATION

CROSS REFERENCE TO RELATED APPLICATION

This application is a continuation in part of application Ser. No. 08/990,828 filed Dec. 15, 1997, now U.S. Pat. No. 5,895,830, the contents of which are hereby incorporated by reference, which is a continuation in part of 08/573,314, filed Dec. 15, 1995, now abandoned, the contents of which are hereby incorporated by reference.

FIELD OF THE INVENTION

This invention relates generally to the production of oligomers from light olefins.

BACKGROUND OF THE INVENTION
Prior Art

Processes for the oligomerization of light olefins to produce $C_7$ and higher carbon number oligomers are well known. Oligomerization processes have been long employed to produce good quality motor fuel components from propylene and butylene. Such oligomerization processes are also referred to as catalytic condensation and polymerization with the resulting motor fuel often referred to as polymer gasoline. Methods have always been sought to improve the octane number of the gasoline boiling range oligomerization products. In addition the oligomerization process is also susceptible to catalyst fouling from the condensation of heavy oligomers into coke that covers the catalyst.

Another process that has met the continuing demand for the conversion of light hydrocarbons into high octane motor fuels was the alkylation of isobutane with propylene, butenes and amylenes using a hydrofluoric acid (HF) catalyst, commonly referred to as HF alkylation. The HF process has provided a highly successful method for the production of high octane motor fuels. Despite a long history of safe operation, recent concerns over the possibility of a catastrophic release of HF acid from HF alkylation units has prompted the investigation of modification or alternatives to the HF alkylation process for the production of motor fuels. One existing alternative is a similar alkylation process that uses sulfuric acid as the catalyst. While the use of sulfuric acid may decrease the degree of the hazard that some associate with the use of HF acid, the sulfuric acid process is still perceived as possibly presenting the same hazard and is not as economically advantageous as the HF alkylation process. Therefore, processing methods have been sought to improve the operation of oligomerization processes as substitutes for acid catalyzed alkylation.

A number of arrangements are known for using oligomerization in combination with other processes such as saturation and dehydrogenation as substitutes for acid catalyzed isomerization alkylation. Patents disclosing the dehydrogenation of light paraffin stream with oligomerization of the dehydrogenation effluent include U.S. Pat. Nos. 4,393,259, 5,049,360, 4,749,820, 4,304,948 and 2,526,966.

It also known to hydrotreat the olefinic hydrocarbon streams produced by oligomerization to saturate olefins. Patent GB 2186287 discloses dehydrogenation of and oligomerization of a C4 fraction to produce a jet aircraft fuel that is optionally hydrogenated into premium gasoline. The hydrotreatment of jet fuels, diesel fuels and lubes produced by dehydrogenation and oligomerization of light paraffins is disclosed in U.S. Pat. No. 4,678,645. However, hydrotreating is not always beneficial for gasoline fractions produced by oligomerization and can lower octane ratings, but is known to be particularly beneficial when saturating isooctenes to isooctanes.

Some prior art process that use highly acidic halide type catalysts for polymerization have suggested the recycle of paraffins to the polymerization zone for purposes of cooling. Such references include U.S. Pat. No. 4,200,714 and U.S. Pat. No. 4,254,294.

It is an object of this invention to improve the operation of an oligomerization reaction zone by extending the catalyst life.

It is a yet further object of this invention to reduce the impact of catalyst fouling by coke accumulation in oligomerization processes.

BRIEF SUMMARY OF THE INVENTION

It has been surprisingly found that the introduction of heavy paraffins into an oligomerization zone for the oligomerization of light olefins by contact with a mild acid catalyst in the oligomerization zone will reduce catalyst fouling and significantly improve the operation of the oligomerization zone. The process introduces a stream of heavy paraffins into the oligomerization zone that contains a mild acid catalyst. The heavy paraffins keep the surface of the catalyst flushed of heavy isomers that can condense and foul the surface of the catalyst. In addition to the inhibition of fouling, the recycling of the heavy paraffins to the oligomerization zone maintains the activity of the catalyst that promotes the selectivity of the oligomerization zone to desired olefins.

While not wishing to be bound to any theory it is believed that the flushing action of the heavy paraffins may be responsible for the improved selectivity of the oligomerization products. Flushing of the catalyst with the heavy paraffin stream maintains a liquid phase flow across the catalyst. The liquid phase flow may be responsible for rapidly removing the initial products from the surface of the catalyst before further reaction can take place to form heavies and cracked products. The oligomerization reaction is highly exothermic so it is believed that the presence of the heavy liquid paraffin also moderates any temperature rise in the reaction zone at large and locally within the catalyst.

A number of specific operational steps can separately or collectively provide the oligomerization improvements of this invention. The flushing benefits of this invention are facilitated by the use of liquid phase conditions and heavier hydrocarbons. Passing heavier hydrocarbons, such as octanes and higher, enhances the improvements of this invention to the oligomerization zone. Furthermore the invention has been proven to raise octane number of gasoline streams substantially when used in conjunction with a mild acid catalyst in the oligomerization zone. Substantial liquid phase conditions in conjunction with the heavy paraffin addition of this invention will offer substantial improvements to the catalyst life, and the catalyst life may be further improved as oligomerization zone approaches 100% liquid phase conditions.

Accordingly in a broad embodiment this invention is an oligomerization process for the production of $C_8$ and higher carbon number olefins. The process passes an oligomerization zone feed comprising $C_3$ and/or $C_4$ olefins to an oligomerization zone and into contact with an oligomerization catalyst at oligomerization conditions with an oligomerization catalyst. The oligomerization catalyst has Hammett acidity function of 4.0 or a lesser acid strength. A heavy saturate stream comprising paraffins having a carbon number of at least 6 passes into contact with the feed and the catalyst. The process recovers an oligomerization effluent stream comprising the paraffins and product oligomers having 8 or more carbon atoms. Useful embodiments may use a milder acid catalyst having a Hammett acidity function of 5.0 or a lesser acid strength. The heavy paraffin stream may comprise $C_8$ and heavier paraffins. The oligomerization zone may be operated to maintain substantial liquid phase conditions.

In another embodiment the process is an oligomerization process for the production of $C_9$ and higher carbon number oligomers. The process passes an oligomerization zone feed comprising $C_3$ and/or $C_4$ olefins to an oligomerization zone and contacts the oligomerization zone feed at oligomerization conditions with a solid phosphoric acid catalyst. A heavy saturate stream comprising $C_6$ and higher carbon number paraffins passes into contact with the feed and the catalyst in the oligomerization zone to maintain at least a portion of the combined heavy saturate stream and feed in liquid phase conditions. The process produces an oligomerization effluent stream comprising the paraffins and product oligomers comprising $C_9$ and higher olefin products. Separation of the oligomerization effluent stream produces an oligomerization product stream comprising product oligomers and recovers at least a portion of the heavy saturate stream comprising the paraffins wherein the highest carbon number of the saturate stream is at least two carbon numbers lower than the lowest carbon number of the product oligomers.

Other objects, embodiments and details of this invention will be provided in the following detailed disclosure of the invention.

DETAILED DESCRIPTION OF THE INVENTION

Figure 1:
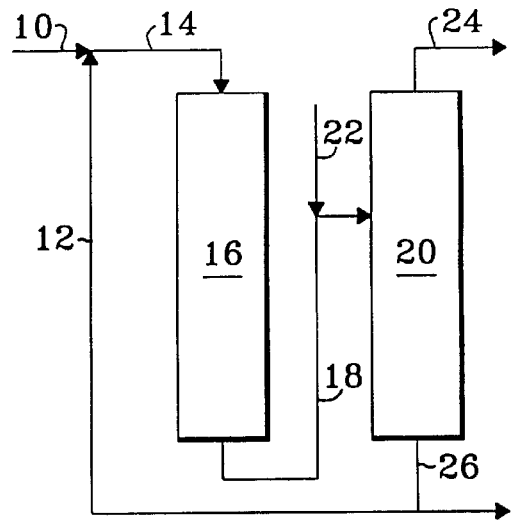
FIG. 1 is process flow diagram showing a basic schematic arrangement of this invention.

The essential operational zone for the practice of this invention is the oligomerization reaction zone. Suitable oligomerization zones for this invention take on many forms. The oligomerization process is known by many names such as catalytic condensation and also catalytic polymerization. Known catalysts for effecting such reactions include heterogeneous catalyst such as solid acids and homogenous catalysts, in particular halogenated catalysts such as boron trifluoride as described in U.S. Pat. Nos. 3,906,053, 3,916,019 and 3,981,941.

Preferred catalyst for the oligomerization reaction can generally be described as mild protonic acids. The preferred acids will generally have a Hammett acidity function of 4.0 or a lower acid strength with Hammett acidity values of 5.0 or more being preferred. Examples of catalysts falling into this category include ion exchange resin catalysts, such as sulfonated ion exchange resins, and phosphoric acid catalysts. A particularly preferred catalyst is a solid phosphoric acid (SPA) catalyst which has a Hammett acidity function of 5.0. The SPA catalyst refers to a solid catalyst that contains as a principal ingredient an acid of phosphorous such as ortho-, pyro- or tetraphosphoric acid.

SPA catalyst is normally formed by mixing the acid of phosphorous with a siliceous solid carrier to form a wet paste. This paste may be calcined and then crushed to yield catalyst particles where the paste may be extruded or pelleted prior to calcining to produce more uniform catalyst particles. The carrier is preferably a naturally occurring porous silica-containing material such as kieselguhr, kaolin, infusorial earth, and diatomaceous earth. A minor amount of various additives such as mineral talc, fuller's earth, and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this composition such as a lower phosphoric acid content are however possible. Further details as to the composition and production of SPA catalysts may be obtained from U.S. Pat. Nos. 3,050,472; 3,050,473; and 3,132,109 and from other references.

Oligomerization zones in general are maintained at conditions which may vary widely due to the previously listed variables. In this invention the oligomerization reaction zone is preferably operated at temperatures and pressures that increase the compatibility of its effluent conditions with the inlet conditions of the saturation reaction zone inlet and its inlet conditions with the dehydrogenation reaction zone effluent conditions. The preferred temperature of the oligomerization reaction zone may be in a range of from 100 to 500° F., will typically be in a range of from 200 to 500° F., and will more typically be in a range of from 300 to 450° F. Pressures within the oligomerization reaction zone will usually be in a range of from 100 to 1200 psig and more typically in a range of from 200 to 1000 psig. When practicing this invention the preferred operating pressure for the SPA catalyst will be in a range of from 100 to 1000 psig and more typically in a range of from 200 to 1000 psig with pressures of 200 to 500 psig being particularly preferred. Oligomerization conditions may also include a liquid hourly space velocity (LHSV) of 0.5 to 5 $hr^{-1}$. It has also been found that maintaining operating temperatures in a narrow range of from 300 to 400° F. can push selectivity toward the production of more $C_8$ isomers.

The feed to the oligomerization zone reaction will typically comprise $C_3$ to $C_5$ olefins and paraffins, but may comprise olefins have carbon numbers of 12 or higher. Steam or water may be fed into the reactor to maintain a low water content for hydration of the preferred SPA catalyst. The source of the olefin feeds are typically a light gas stream recovered from the gas separation section of an FCC process, $C_4$ streams from steam cracking and coker off gas or the effluent from dehydrogenation zone. The olefin feed stream is characterized by having an overall $C_4$ olefin concentration of at least 10 wt %. In most operations, this olefin feed stream will contain $C_4$ olefins but it may also constitute all or substantial quantities of $C_3$ olefins. Typically the olefin feeds can have a $C_3$ to $C_5$ olefin concentration of at least 30 wt %. The principal oligomerization products comprise $C_8$ and heavier olefins. The principal reaction substrate in the reaction zone will comprise propylene or normal butene. Where $C_3$ olefins are present as feed, these olefins will primarily combine to produce $C_9$ and higher alkenes. Preferred feeds will have a concentration of at least 30 wt % and more preferably at least 50 wt % total olefins in the feed stream. The olefin content of the feed may predominately comprise normal olefins of a single carbon number.

In the practice of this invention heavy paraffin components contact the catalyst in conjunction with the usual oligomerization zone feed. The heavy paraffin components will comprise hydrocarbons having at least six carbon atom, preferably at least seven carbon atoms, and more preferably at least 8 carbon atoms. Paraffin components having up to twenty carbon atoms may be used and will preferably comprise paraffins having a substantially different carbon number than the product oligomers.

The presence of the heavy paraffins promotes liquid phase conditions in the oligomerization zone. The combined heavy saturate stream and feed will usually maintain at least partial liquid phase conditions in the oligomerization zone. The term "partial liquid phase conditions" refers to maintaining at least 10 wt % of the combined heavy saturate stream and feed in liquid phase. Preferably at least 50 wt % of the combined feed and heavy saturate stream are in liquid phase in the oligomerization zone to provide substantial liquid phase conditions, and more preferably essentially all, i.e. at least 90 wt %, of the fluid in the oligomerization zone will be in liquid phase.

The effective washing action of the heavy hydrocarbons requires a minimum liquid mass flux. Preferred rates for the liquid mass flux will exceed 3000 lb/hr/ft$^2$. The effectiveness of the liquid mass flux may be improved by the incorporation of a suitable inlet distributor at the top of the reactor. For multi-bed reactors the use of an inlet distributor in the first reactor may be the most critical because of the significant amount of reaction that takes place in that reactor.

The heavy paraffin components may enter the process with the incoming feed or may be injected into an oligomerization reaction zone at intermediate locations within a single catalyst bed or a number of catalyst beds. It is preferred to have the heavy paraffins present as the feed initially enters the reaction zone to maximize the benefit of the heavy paraffins in the process. In such cases it is typical to have at least 40 wt % and more often 50% or more of the total cycloparaffin stream enter the first reactor with the feed. Additional quantities of the heavy paraffins may be injected in stages through the process to maintain temperature control throughout the bed or beds of oligomerization catalyst.

Where the oligomerization zone has a multiple bed arrangement, the different catalyst beds are preferably contained within one or more cylindrical, vertically oriented vessels and the feed stream preferably enters the top of the reactor. The catalyst is preferably disposed in fixed beds within the oligomerization zone in what is known as a chamber-type reactor structure. Typically, a chamber-type reactor will contain about five catalyst beds. In a chamber-type reactor, the reactants flow through a series of large diameter catalyst beds. The temperature of the reactants may be further controlled by recycling additional relatively inert hydrocarbons to act as a heat sink. Oligomerization reaction zones are routinely arranged with such multiple beds of catalyst that receive an intermediate injection of a quench material to control temperatures from the exothermic reaction. Substantial advantage can be obtained by adding the heavy paraffin feed as an intermediate injection stream that also benefits the process by serving as a quench stream.

With the addition of the heavy paraffin stream the combined feed to the oligomerization zone will preferably have a ratio of light and heavy paraffins to olefms of from 1:1 to 5:1. Thus the overall paraffin concentration of the feed to the oligomerization reaction zone will typically be at least 50 wt % and more typically at least 70 wt %. A high percentage of the olefins in the feed stream are reacted in the oligomerization reaction zone along with the isobutene. The olefin conversion will typically range of from 80 to 99 wt %.

The effluent from the oligomerization reaction zone will normally enter a separator. Separation of the effluent stream from the oligomerization zone will at minimum recover the heavy paraffins from the effluent for recycle to the oligomerization zone. The usual separator for recovery of the product oligomers also recovers unreacted feed as an overhead stream and at least a portion of the heavy saturate stream for recycle to the oligomerization zone. The paraffins for recycle may be recovered with the product stream or the unreacted feed olefins.

Where product recovery limits the bottom capacity of existing fractionation zones, paraffins with lower carbon numbers than the product oligomers are preferred. Relatively lower carbon number paraffins may be recovered overhead with unreacted feed components for combined recycle back to the oligomerization zone. Where column flooding limits overhead recovery of relatively lighter paraffins, it may be beneficial to recover a recycle paraffin stream as a sidecut.

Addition of a heavy paraffin stream will provide a substantial quantity of heavy paraffins in the oligomerization zone and preferably will produce a minimum of 20 wt % $C_6$ and heavier paraffins in the reactor effluent stream and will more typically produce at least 15 wt % of $C_6$ and heavier paraffins at the inlet of each catalyst bed in the reaction zone. C8 paraffins are particularly preferred and will preferably comprise at least 10 to 30 wt % of the mass flow through the oligomerization reaction zone. In many cases the weight ratio of heavy saturate to the olefin feed is in a range of from 0.5 to 4 and more often in a range of from 1 to 2.

Separating $C_8$ paraffins from the effluent stream for recycle may bring some heavy olefins into the recycle stream and require saturation of the reactive olefins before they are returned to the oligomerization zone. Circulation of the paraffins through the process and carryover of heavy olefins will produce some quantity of heavy oligomers. Therefore, a source of heavy paraffins is needed to supply the initial paraffms for circulation in the recycle stream as well as make-up paraffms for circulation through the process. Additional make-up paraffins are usually combined with the recycled heavy paraffins to make up for losses in the heavy paraffin stream. The paraffins may be lost with product oligomers or purposefully purged as a small drag stream to maintain a sufficiently low concentration of contaminants in the paraffin recycle. The concentration of heavy oligomers in the recycle stream is kept low by purging a portion of the effluent stream from the bottoms stream of the separator.

The source of the heavy paraffins to the oligomerization zone can be any stream that can supply the higher carbon number paraffins in the necessary quantities. The paraffins can be imported into the process from external sources or produced by saturating all or a portion of the oligomerization effluent stream. (Unless otherwise noted the term "portion" when used herein to describe a process stream refers to either an aliquot portion of the stream or a dissimilar fraction of the stream having a different composition than the total stream from which it was derived.) The entire effluent from the oligomerization zone may be saturated to provide a source of recycle paraffins for the process as well as saturated oligomers. Or the effluent may be separated as described to recover the portion of the paraffins that are recycled to the oligomerization zone.

Providing at least a two carbon number difference between the paraffin stream and the product oligomers will simplify separation and recovery of the paraffin recycle. For example where the product oligomers comprise $C_9$, oligomers the heavy saturate stream will comprise $C_7-$ or $C_{11}+$ paraffins. A particularly useful recycle stram for supplying relatively lighter paraffins is an isomerate stream that is rich in $C_6$ and higher saturates saturates and relatively free of any unsaturates. To facilitate separation of isomerate type paraffin streams at least 50 wt % of the product olefins will comprise hydrocarbons that are at least two carbon numbers higher than at least 50 wt % of the heavy saturate stream.

Figure 2:
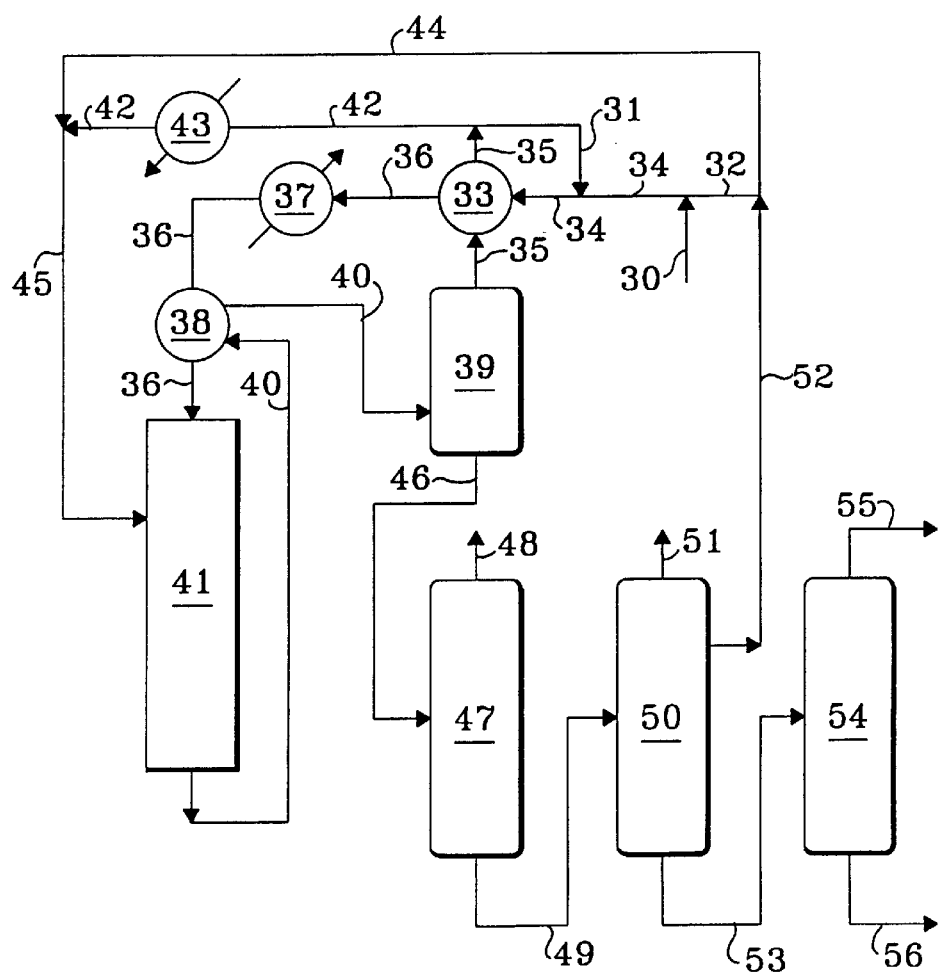
FIG. 2 is process flow diagram showing an alternate arrangement for the process of this invention.

The process and different operational steps will be described in conjunction with FIGS. 1 and 2. FIGS. 1 and 2 show only limited forms of the invention and only those portions of the process that are necessary to gain an understanding of the invention and the necessary means of integrating the principal processing steps that comprise the invention. Further details related to valves, control means, pumps, compressors, coolers, and other necessary processing equipment are well known to those skilled in the art and not described in detail unless necessary for an understanding of the invention.

Turning then to FIG. 1, an oligomerization zone feed stream, rich in $C_4$ olefins is brought into the process by a line 10 and combined with a recycle stream of $C_{12}$ paraffins carried by a line 12. A line 14 carries the combined feed and recycle paraffin stream into an oligomerization reaction zone 16 wherein the feed and paraffins contact an SPA catalyst. A stream 18 carries an oligomerization effluent comprising $C_8$ olefins and $C_{12}$ paraffins to a separator 20. A line 22 adds a make-up stream of $C_{12}$ paraffins to the effluent entering separator 20. Separator 20 removes a heavy fraction containing $C_{12}$ paraffins from the $C_8$, oligomers formed in the oligomerization zone. Separator 20 may provide a simple flashing operation to make a rough cut of the heavy stream or may be a fractionation zone. An overhead stream 24 carries the $C_8$ olefins from separator 20 for further processing. Such further processing may include saturation of the olefins in a saturation zone. A bottoms stream containing $C_{12}$ paraffins for recycle to the process is withdrawn by a line 26. A good separation is desired to minimize the carry-over of $C_{12}$ olefins to the oligomerization zone. A portion of the bottoms stream in line 26, which is typically equal to the mass flow of the make-up paraffin addition from line 22, is purged from the process to reduce the build up of heavy oligomers in the recycle stream. The remainder of the heavy paraffins is returned for admixture with incoming feed via line 12.

In the arrangement of FIG. 2 an oligomerization zone feed stream, rich in $C_3$ olefins is brought into the process by a line 30 and combined with a recycle stream of $C_6$ and heavier paraffins carried by a line 32. A line 34 carries the combined feed and recycle paraffin stream into an oligomerization reaction zone and into optional combination with light olefins from a line 31. An exchanger 33 heats the feed against a stream 35 of flashed vapors from the overhead of a flash drum 39. A line 36 passes the combined feed through a heater 37 and an effluent exchanger 38 to raise the combined feed to its initial reaction temperature. The combined feed, including the heavy paraffins, contacts an SPA catalyst in a multi-bed reactor 41. A line 42 carries flashed overhead vapor through a condenser 43. The overhead stream will usually comprise $C_3$ and lighter hydrocarbons including unreacted feed olefins and light paraffins. Condenser 43 prepares the flash overhead for introduction as a quench into one or more of the catalyst beds of reactor 41. A line 45 introduces the quench into reactor 41 together with any optional addition of heavy paraffins from a line 44.

Line 40 delivers the oligomerization effluent for heat and product recovery. The effluent contains unreacted feed olefins, light and heavy paraffins, and oligomers. After cooling against the incoming feed in exchanger 38, the mixed contents of line 40 enter flash drum 39 in mixed phase. Flash drum 39 produces an overhead stream rich in $C_3$ olefins and lower boiling hydrocarbons that is recycled to reactor 41 as previously described. Line 46 carries bottoms liquid containing absorbed light hydrocarbons to a fractionation zone for removal of a net propane stream via a line 48. Bottoms from fractionator 47 enter a fractionator 50. Fractionator 50 maintains a cut point between lighter hydrocarbons and the heavy paraffin recycle by withdrawing an overhead 51 comprising mainly $C_4$ hydrocarbons and a sidecut stream 52. Sidecut stream 52 comprising mainly $C_6$ paraffins for recycle to the reaction zone as previously described. Sidecut 52 may also contain $C_6$ olefins that undergo further combination to produce more product oligomers. The remaining heavier fraction of the effluent consists mainly of heavier trimers and tetramers that pass to fractionator 54. Fractionator 54 recovers the $C_9$ trimers overhead via line 55 while $C_{12}$ tetramers and higher oligomers leave the process through bottom stream 56.

To more fully demonstrate the attendant advantages of the present invention, the following tests were performed.

EXAMPLE 1

A feedstream having a composition of 13 wt % normal butene, 17.7 wt % isobutene and 69.4 wt % isobutane was contacted with about 50 cc of a solid phosphoric acid catalyst comprising a calcined mixture of phosphoric acid in siliceous base. The catalyst comprised pellets approximately ¼" in diameter and length that were retained in a ⅞" steel reactor vessel having a volume of 70 cc. Channeling was avoided by carefully sand packing the void volume between particles. The feed entered the reactor at a temperature of 374° F. and a pressure of 500 psig and passed through the reactor at a liquid hourly space velocity of 2. The oligomerization reaction produced a maximum reactor temperature of 396° F. A sample of the reactor effluent was recovered, distilled and analyzed to determine the conversion of $C_4$ olefins and the carbon number selectivities of the products. The results of the analysis are shown in Table 1.

TABLE 1

| FEED | CONV. % | CARBON NO. SELECTIVITIES, WT % | | | | |
|---|---|---|---|---|---|---|
| | | 5—>7 | 8 | 9—>11 | 12 | >12 |
| EX- AMPLE 1 | n-$C_4^-$ = 85 iso-$C_4^-$ = 91 TOTAL $C_4^-$ = 88 | 8.4 | 56 | 5.2 | 28 | 2.4 |
| EX- AMPLE 2 | n-$C_4^-$ = 81 iso-$C_4^-$ = 91 TOTAL $C_4^-$ = 86 | 4.7 | 66.2 | 3.9 | 24.6 | 0.6 |

EXAMPLE 2

In order to demonstrate the advantages of a heavy recycle an additional 25 wt % of normal $C_8$ paraffins were added to the feed of Example 1 and run at the operating conditions and with the same catalyst as Example 1. The oligomerization zone reached a maximum temperature of 392° F. A sample of the effluent from the reaction zone was again distilled and analyzed and found to contain a significantly higher percentage of $C_8$ olefins. The results of the analysis are again shown in Table 1.

Comparison of Examples 1 and 2 demonstrates that at approximately equal $C_4$ olefin conversions the addition of the $C_8$ paraffins shifted the selectivity of the reactor effluent significantly toward the production of the highly desired $C_8$ isomer and surprisingly away from the production of both higher and lower carbon number isomers.

As this example demonstrates, the recycle stream of this invention provides a significant improvement in the selectivity of the oligomerization to high octane $C_8$ isomers.

EXAMPLE 3

A feedstream having a composition of 8.4 wt % normal butene, 21.9 wt % isobutene and 69.7 wt % isobutane was contacted with about 50 cc of a solid phosphoric acid catalyst of the type used in Examples 1 and 2. The reactor vessel and catalyst loading technique was also of the same type used in Examples 1 and 2. Feed entered the reactor at a temperature of 376° F. and a pressure of 500 psig and passed through the reactor at a liquid hourly space velocity of 2. The oligomerization reaction produced a maximum reactor temperature of about 403° F. A sample of the reactor effluent was recovered hydrogenated, distilled and analyzed to determine the conversion of $C_4$ olefins, the carbon number selectivities of the products and the research and motor octane number. The results of the analyses are shown in Table 2.

TABLE 2

| FEED | TEMP ° F. INLET/MAX | LHSV, HRS$^{-1}$ | CONV. % | CARBON NO. SELECTIVITES, WT % | | | | | RON | MON |
|---|---|---|---|---|---|---|---|---|---|---|
| | | | | 5->7 | 8 | 9->11 | 12 | >12 | | |
| EXAMPLE 3 | 376/403 | 2 | n-$C_4^-$ = 83 iso-$C_4^-$ = 94 TOTAL $C_4^-$ = 91 | 10.5 | 51 | 6 | 30 | 2.5 | 83.3 | 84.6 |
| EXAMPLE 4 | 308/322 | 2 | n-$C_4^-$ = 54.5 iso-$C_4^-$ = 96.5 TOTAL $C_4^-$ = 87 | 0.8 | 87.2 | 0.3 | 11.7 | — | 101 | 95.0 |
| EXAMPLE 5 | 320/340 | 2 | n-$C_4^-$ = 63.7 iso-$C_4^-$ = 95.9 TOTAL $C_4^-$ = 88.7 | 1.3 | 83.1 | 0.9 | 14.7 | — | 99.7 | 94.7 |
| EXAMPLE 6 | 329/338 | 0.75 | n-$C_4^-$ = 83 iso-$C_4^-$ = 96.5 TOTAL $C_4^-$ = 94 | 2.3 | 75.3 | 1.6 | 20.8 | — | 97.9 | 93.2 |

EXAMPLES 4–6

In order to demonstrate the advantages of a heavier components than $C_8$ and lower operating temperatures an additional 25 wt % of normal $C_{12}$ paraffins were added to the feed of Example 3 and run at a range of reduced operating temperatures and space velocities with the same catalyst as Example 3. Conversions, selectivity and research and motor octane numbers after distillation and hydrogenation of effluents from the three runs with the added $C_{12}$ components to the feed are shown in Table 2 as Examples 4–6.

All three of the runs operated with reduced temperatures relative to Example 3 and show significant improvement to the $C_8$ selectivity by the addition of the normal $C_{12}$ paraffins. Examples 4 and 5 both demonstrate a much higher selectivity to $C_8$ isomers than Example 3 at an only slightly reduced conversion. The improved selectivity resulted in a much higher octane number than that obtained without the $C_{12}$ components in Example 3. Example 6 demonstrates that higher conversions than Example 3 may be obtained at relatively higher temperatures and a reduced space velocity while still maintaining a significantly higher selectivity to $C_8$ isomers than shown in Example 3.

What is claimed is:

1. An oligomerization process for the production of $C_8$ and higher carbon number olefins, said process comprising:
   a) passing an oligomerization zone feed comprising $C_3$ and higher olefins to an oligomerization zone and contacting the oligomerization zone feed at oligomerization conditions with an oligomerization catalyst having a value of 4.0 or more for a Hammett acidity function;
   b) passing a heavy saturate stream comprising paraffins having a carbon number of at least 6 into contact with said feed and said catalyst; and,
   c) recovering an oligomerization effluent stream comprising said paraffins and product oligomers having 8 or more carbon atoms.

2. The process of claim 1 wherein the oligomerization conditions include a temperature of 200 to 500° F., a pressure of 100 to 1000 psig, and an LHSV of 0.5 to 5.

3. The process of claim 1 wherein said oligomerization zone operates at a temperature in a range of from 300 to 450° F.

4. The process of claim 1 wherein said oligomerization effluent stream is passed to a separator and separated into a product stream comprising $C_8$ or higher carbon number olefins and said heavy saturate stream, at least a portion of said heavy saturate stream is recycled to said oligomerization zone, a portion of said heavy saturate stream is rejected from the process and a heavy paraffin stream is combined with said oligomerization zone to provide make up paraffins for said heavy saturate stream.

5. The process of claim 1 wherein at least a portion of said heavy saturate stream enters said oligomerization zone with the feed.

6. The process of claim 1 wherein at least 50 wt % of the product olefins comprise hydrocarbons having carbon numbers at least two carbon numbers higher than at least 50 wt % of the heavy saturate stream.

7. The process of claim 1 wherein the weight ratio of heavy saturate to olefin feed is in a range of from 0.5 to 4.

8. The process of claim 7 wherein at least 40 wt % of the heavy saturate stream enters the oligomerization zone with the incoming feed.

9. The process of claim 1 wherein the product oligomers comprise $C_9$ oligomers and the heavy saturate stream comprises $C_7$ paraffins.

10. The process of claim 1 wherein the saturate stream comprises paraffins having a carbon number of at least 7.

11. The process of claim 1 wherein said oligomerization zone catalyst comprises a protonic acid having a value of 5.0 or more for a Hanmmett acidity function.

12. The process of claim 1 wherein said oligomerization zone catalyst comprises a solid phosphoric acid catalyst.

13. The process of claim 1 wherein said heavy saturate stream comprises $C_8$ to $C_{20}$ paraffins.

14. An oligomerization process for the production of $C_9$ and higher carbon number oligomers, said process comprising:
   a) passing an oligomerization zone feed comprising $C_3$ and/or $C_4$ olefins to an oligomerization zone and contacting the oligomerization zone feed at oligomerization conditions with a solid phosphoric acid catalyst; b) passing a heavy saturate stream comprising $C_6$ and higher carbon number paraffins into contact with said feed and said catalyst to the oligomerization zone to maintain at least a portion of the combined heavy saturate stream and feed in liquid phase conditions in the oligomerization zone;
   c) recovering an oligomerization effluent stream comprising said paraffins and product oligomers comprising $C_9$ and higher olefin products; and,
   d) separating said oligomerization effluent stream to produce an oligomerization product stream comprising product oligomers and to recover at least a portion of the heavy saturate stream comprising said paraffins wherein the highest carbon number of the saturate stream is at least two carbon numbers lower than the lowest carbon number of the product oligomers.

15. The process of claim 14 wherein the product oligomers comprise $C_9$ olefins and the oligomerization product stream contains less than 2 wt % of $C_8$ and lower hydrocarbons.

16. The process of claim 14 wherein said heavy saturate stream is recovered as a sidecut stream from a separator.

17. The process of claim 14 wherein makeup paraffins are added to said heavy recycle stream.

18. The process of claim 14 wherein the oligomerization conditions include a temperature of 200 to 500 ° F., a pressure of 100 to 1000 psig, and an LHSV of 0.5 to 5.

19. The process of claim 14 wherein the oligomerization zone is maintained in a substantial liquid phase.

20. The process of claim 19 wherein at least 50 wt % of the oligomerization effluent exits the oligomerization zone in liquid phase.

21. The process of claim 14 wherein at least a portion of said heavy saturate stream enters said oligomerization zone with the feed.

22. The process of claim 14 wherein at least 50 wt % of the product oligomers comprise olefins having carbon numbers at least two carbon numbers higher than at least 50 wt % of the heavy saturate stream.

23. The process of claim 14 wherein the weight ratio of heavy saturate to olefin feed is in a range of from 0.5 to 4.

24. The process of claim 14 wherein the saturate stream comprises paraffins having a carbon number of at least 7.

* * * * *